United States Patent
Zimmermann et al.

(10) Patent No.: US 8,240,419 B2
(45) Date of Patent: Aug. 14, 2012

(54) ALCOHOL INTERLOCK SYSTEM WITH WIRELESS DATA TRANSMISSION AND SAFETY FUNCTION

(75) Inventors: Martin Zimmermann, Hamburg (DE); Stefan Morley, Lübeck (DE); Michael Reinhart, Stockelsdorf (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 150 days.

(21) Appl. No.: 12/772,464

(22) Filed: May 3, 2010

(65) Prior Publication Data

US 2010/0314190 A1 Dec. 16, 2010

(30) Foreign Application Priority Data

Jun. 16, 2009 (EP) .................................... 09162775

(51) Int. Cl.
*B60K 28/06* (2006.01)
*G01N 33/497* (2006.01)
(52) U.S. Cl. .............. 180/272; 340/576; 73/23.3; 701/1
(58) Field of Classification Search .................. 180/272; 340/576; 73/23.3; 701/1
See application file for complete search history.

(56) References Cited

U.S. PATENT DOCUMENTS

| | | | |
|---|---|---|---|
| 6,748,792 B1 | 6/2004 | Freund et al. | |
| 7,256,700 B1 | 8/2007 | Ruocco et al. | |
| 7,823,681 B2 * | 11/2010 | Crespo et al. | 180/272 |
| 2003/0036823 A1 * | 2/2003 | Mahvi | 701/1 |
| 2004/0138823 A1 * | 7/2004 | Gollar | 702/19 |
| 2005/0241871 A1 * | 11/2005 | Stewart et al. | 180/272 |
| 2006/0202842 A1 | 9/2006 | Sofer | |
| 2007/0273537 A1 | 11/2007 | Crespo et al. | |

FOREIGN PATENT DOCUMENTS

| | | |
|---|---|---|
| DE | 197 42 261 | 4/1999 |
| WO | WO 2009/048809 | 4/2009 |

* cited by examiner

*Primary Examiner* — Joseph Rocca
*Assistant Examiner* — Keith Frisby
(74) *Attorney, Agent, or Firm* — McGlew and Tuttle, P.C.

(57) ABSTRACT

An interlock system (1) for a vehicle is provided with an alcohol tester (4), which is designed to measure the alcohol level of a driver of the vehicle. A control device (2) is coupled with the alcohol tester (4) and is designed to make it possible to start the vehicle or to prevent the vehicle from being started depending on the measured alcohol level. A transceiver module (3) is coupled with the control device (2) and is designed to send data to a remotely located control system in a wireless manner or to receive data from said control system in a wireless manner. The transceiver module (3) is designed, furthermore, to release the control device (2) in response to data received in a wireless manner in order to make it possible to start the vehicle regardless of the operating state of the control device.

20 Claims, 2 Drawing Sheets

ALCOHOL INTERLOCK SYSTEM WITH WIRELESS DATA TRANSMISSION AND SAFETY FUNCTION

CROSS REFERENCE TO RELATED APPLICATIONS

This application claims the benefit of priority under 35 U.S.C. §119 of European Patent Application EP 09 162 775.2 filed Jun. 16, 2009, the entire contents of which are incorporated herein by reference.

FIELD OF THE INVENTION

The present invention pertains to a device that is designed to prevent a vehicle from being started or a machine from being operated by a user who is under the influence of alcohol. Such a device is usually called an alcohol interlock system or "interlock" for short and embodies, in general, the combination of an alcohol tester as well as a vehicle immobilizer for a motor vehicle or a blocking means for a machine.

BACKGROUND OF THE INVENTION

An interlock system is usually used to prevent a driver who is under the influence of alcohol after a positive result has been obtained for an alcohol test from starting the engine of a vehicle (passenger car, truck, bus, etc.). An interlock system contains for this essentially two components: An alcohol tester, which is usually located inside the vehicle, as well as a control device, which is coupled with the alcohol tester and is permanently installed, for example, under the dashboard of the vehicle and is designed to connect or block the power supply to the starter of the vehicle. The alcohol tester is preferably a breath alcohol tester that is designed as a hand-held device and is connected to the control device via an electric connection cable. As an alternative, the hand-held device may also be coupled with the control device in a wireless manner (for example, via infrared light, Bluetooth or similar protocols).

Such an interlock system usually operates as follows: After switching on the vehicle's ignition, the interlock system prompts the driver to give a breath sample. The test result for the measured breath alcohol concentration, from which the alcohol level can be determined by means of known algorithms, decides whether the starter of the vehicle is released and the engine can be started.

Tampering is possible, in principle, when using an interlock system because, for example, a requested alcohol test is performed by a second person, who is not the driver who is to be checked. To rule out such a possibility of evasion, prior-art interlock systems usually have an alcohol test repeat function. This means that the interlock system prompts the driver again after a randomly generated time interval to perform an alcohol test.

To determine the breath alcohol concentration or the alcohol level, the testing system of an interlock system normally contains an electrochemical sensor system, as it is also used in breath alcohol testers used by the police. This sensor system responds very specifically to alcohol, so that other expired substances or cigarette smoke do not distort the test result.

All the events relevant for the use, for example, date, time, release of a breath sample or refusal to release a breath sample, measured alcohol concentration, engine starts and engine stops, electric bypassing of the interlock system as well as other attempts at tampering are recorded in a memory of the interlock system during the use of the vehicle. These data can be compiled into a protocol and read, for example, by means of a data cable, by which the hand-held device of the interlock system is connected to an external computer. The reading may take place, for example, in an authorized workshop or on site by an authorized mechanic.

DE 197 42 261 A1 describes a device for blocking the operation of a vehicle by a driver who is under the influence of alcohol. The alcohol tester is designed to be attached to a body part (arm or leg) of the driver and to be able to measure the driver's alcohol level by means of an electrochemical gas sensor via the skin permeation. The analyzing unit of the device proper, via which release or blocking of the vehicle takes place, is mounted permanently in the vehicle and communicates with the tester in a wireless manner.

U.S. Pat. No. 7,256,700 B1 pertains to an interlock system, by means of which a vehicle is prevented from being started by a driver who is under the influence of alcohol. The interlock system is coupled with a cell phone or a similar communications means, with which a failed alcohol test is communicated by a verbal message being sent via the cell phone. Furthermore, data, which are stored in the interlock system, can also be sent via the cell phone.

US 2007/0273537 A1 discloses a combined testing and positioning system, which contains, among other things, an interlock system. The interlock system is used in this case in the known manner to prevent a vehicle from being started by a driver who is under the influence of alcohol. The system is equipped, furthermore, with an EMHA (Electronic Monitoring Home Arrest) system, which can communicate with a remote server, for example, via a cell phone. However, data being stored in the interlock system can be communicated to the server via this cell phone as well.

One drawback of the prior-art interlock systems is that these cannot be deactivated or reactivated from a remote center. Many interlock systems are not used to prevent, for example, an offender sentenced because of an alcohol-related offense, from starting his automobile while under the influence of alcohol. Many interlock systems are rather used on a voluntary basis or are used to increase safety, for example, in areas of the transport of heavy loads, the transport of hazardous materials, in school buses, in tourist buses or even in public or private passenger transportation. Should the vehicle be prevented from being started, for example, because of a technical defect of the interlock system or due to a malfunction of or erroneous detection by the alcohol sensor, the driver is not able to start his or her vehicle even though the driver is not under the influence of alcohol.

As was explained above, the driver of a vehicle is usually prompted by the interlock system to perform an alcohol test not only at the beginning of a drive but also during the drive at irregular and randomly determined time intervals. It may therefore happen in case of a sudden malfunction of the interlock system that, for example, a truck transporting hazardous materials cannot be started any more in the middle of the turnpike. The defective interlock system can be released or deactivated in such a case on site only at the interlock system of the vehicle itself by a specially trained and authorized mechanic driving to the "stopped" vehicle and entering a secret release code into the interlock system via a data cable with the corresponding interface of the interlock system, as a result of which the interlock system is released or deactivated and the engine of the vehicle can again be started without a repeated alcohol test being performed. (However, this is possible only if there is no hardware defect, which makes communication with the interlock entirely impossible.) The interlock system must subsequently be repaired and reactivated in a workshop. Should no mechanic be available, the vehicle must be towed to an authorized repair shop in order to have the interlock system released or deactivated there. Both solutions are very time-consuming and lead to high resulting costs.

SUMMARY OF THE INVENTION

The basic object of the present invention is therefore to provide an interlock system by means of which the above-mentioned drawbacks are overcome. In particular, it is the object of the present invention to provide an interlock system that is designed to prevent a vehicle from being started or a machine from being operated by a driver/user who is under the influence of alcohol and is designed to transmit data being stored in the interlock system in a wireless manner to a remotely located control system and/or to transmit data from a remotely located control system to the interlock system in a wireless manner.

Another object of the present invention is to deactivate (release or bypass) and/or reactivate the interlock system from a remotely located control system in a wireless manner.

According to the invention, an interlock system is provided for a vehicle. The interlock system comprises an alcohol tester for measuring an alcohol level of a driver of the vehicle and a control device coupled with the alcohol tester for allowing starting of the vehicle or preventing the vehicle from being started depending on the measured alcohol level. The interlock system also includes a transceiver module coupled with the control device for sending data to a remotely located control system in a wireless manner and for receiving data from the control system in a wireless manner. The transceiver module releases the control device in response to data received in a wireless manner in order to allow starting of the vehicle regardless of the operating state of the control device.

As was explained above, an interlock system is an alcohol tester with vehicle immobilizer. The alcohol testing is usually performed as a breath alcohol test, but this is not a necessary condition for the interlock system according to the present invention. Other methods of alcohol testing (for example, testing of the alcohol concentration via skin permeation) may also be used, in principle, for the interlock system according to the present invention. The object of the interlock system according to the present invention is to prevent a driver who is under the influence of alcohol from starting the engine of the vehicle in which the interlock system is installed. Alcohol-related accidents can be prevented by the installation of the interlock system. Furthermore, the interlock system is suitable for supporting long-term changes in the driver's behavior towards alcohol.

The practical procedure is generally such that the driver of the vehicle is prompted by the interlock system to perform a breath alcohol test in case of an attempt at starting the vehicle. Depending on the result of this test (i.e., the alcohol level), the signal chain to the engine's starter is released and it is made possible for the driver to start the engine.

All relevant operations in connection with the use of the interlock system in a vehicle are stored in a memory of the interlock system. This memory can be read at any desired point in time by persons or institutions authorized to do so. The reading of the memory is performed, for example, in connection with programs for drunk drivers at regular intervals (e.g., once a month) in authorized service workshops. The data are then processed by data management software, and the relevant information is then transmitted (e.g., via e-mail, SMS, cell phone or fax) to a monitoring office (e.g., probation officer).

Furthermore, it is possible to shorten the "service period" if certain events (e.g., a failed breath test) occur in order to thus prompt a premature visit to a service workshop.

A technical defect of the interlock system may cause, in principle, the vehicle not being able to be started any more. The interlock system usually must be bypassed in this case. This may mean that the vehicle must be towed to a service workshop for this and that a technician must drive to the stopped vehicle in order to correct the defect or to bypass the interlock functionality.

As was explained above, the memories of prior-art interlock systems can be read at regular intervals only, for example, in a service workshop. Therefore, there is a time delay (for example, 4 weeks) between the recording of misconduct in the memory and the information of monitoring offices or regulatory authorities. The advantage of the interlock system according to the present invention is that this time delay can be shortened in order to thus make possible a quicker reaction to a misconduct of the driver and/or in order to grant direct access to the data being stored in the interlock system to an authorized person (e.g., probation officer). This advantage is made possible to a wireless communication between the interlock system and a remotely located control system.

Another advantage of the interlock system according to the present invention is that continued driving of the vehicle can be made possible in case of a technical defect of the interlock system and/or that certain maintenance tasks can be performed on the interlock system without having to drive to a service workshop therefor. It is important in this connection that the bypassing of the interlock functionality cannot be brought about by the driver alone for continued travel, but at least one authorized releasing person or institution is involved. The release or deactivation of the interlock system and the subsequent reactivation thereof likewise take place by a wireless communication between the interlock system and the authorized person or institution, who has access to the control system. The control system, or generally target system, may be a data bank accessible through a computer or simply a cell phone or fax machine. It is likewise achieved by means of the present invention that especially the releasing functionality is not part of the (potentially defective) interlock system in case of a defective interlock system but this releasing functionality is adapted to the interlock system.

The present invention was generally described above for the application in a motor vehicle. However, it should be understood that the interlock system according to the present invention can likewise be used to block the operation of a machine by a user who is under the influence of alcohol. Examples of such a machine are large construction equipment, machines in industrial/chemical production plants or power plants, etc.

The present invention will be described now on the basis of an example for application in a motor vehicle with reference to the FIGURE. The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

DESCRIPTION OF THE PREFERRED EMBODIMENTS

Figure 1:
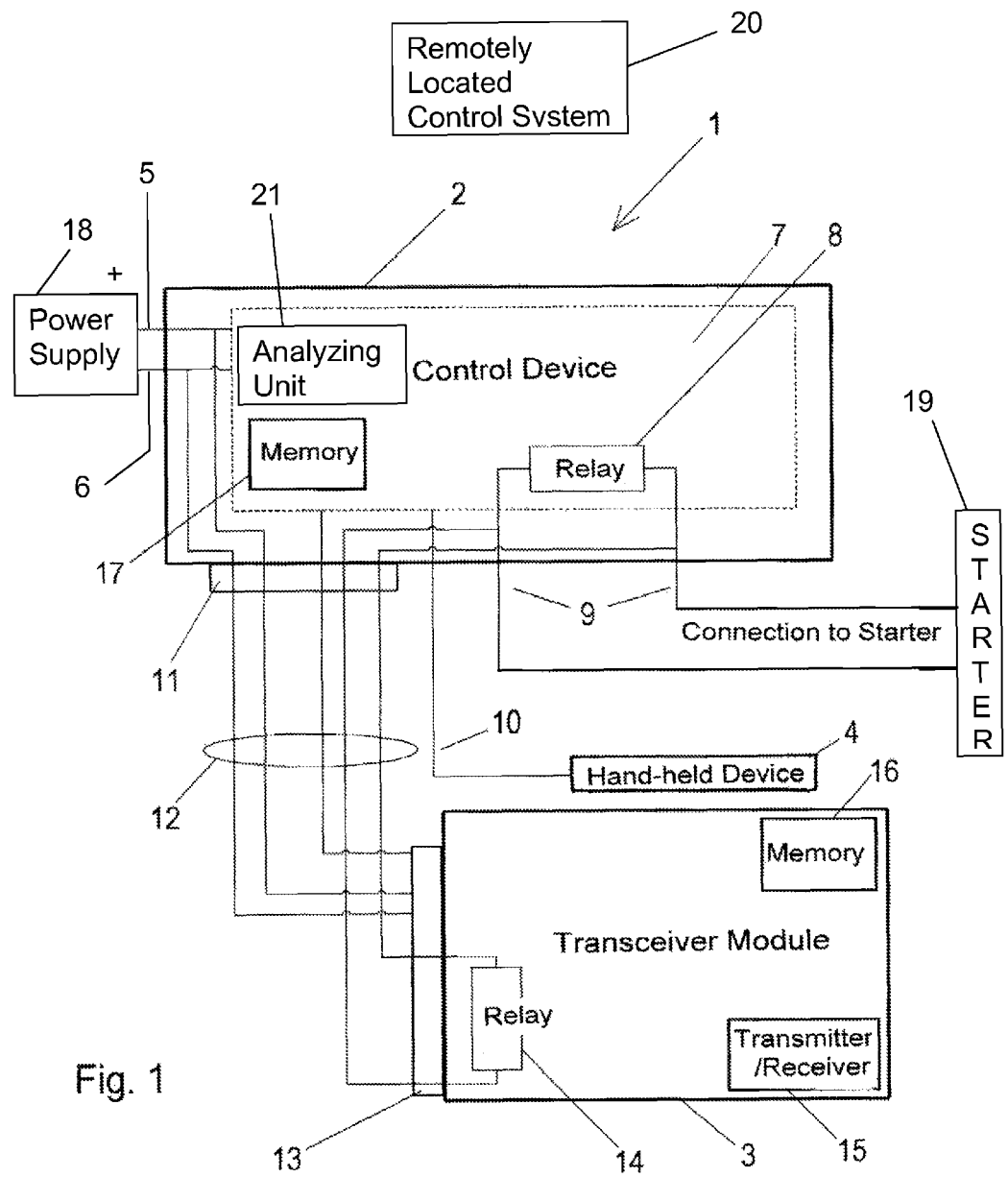
FIG. 1 is a block diagram of the interlock system according to the present invention.
Figure 2:
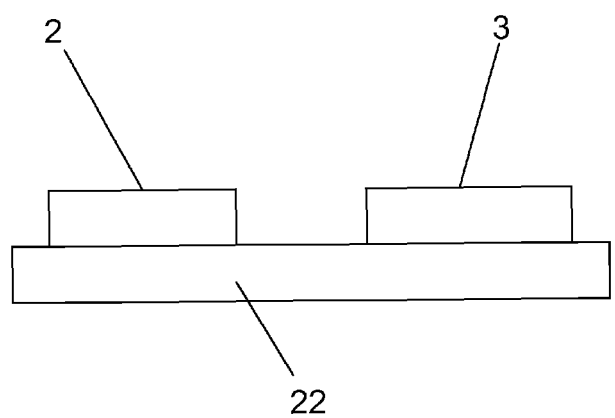
FIG. 2 is a side view of a transceiver module and a control device provided on a printed circuit board.

Referring to the drawings in particular, an interlock system 1 shown in FIG. 1 has essentially a control device 2 coupled with the ignition of a motor vehicle, a module 3 for wireless data transmission and a hand-held device 4 for alcohol testing. The control device 2 is connected via two terminals 5, 6 to the battery or power supply 18 of the vehicle, in which the interlock system 1 is installed. The components of the control device are contained in a stable housing, which is mounted preferably under the dashboard of the vehicle or in another, difficult-to-access and safe area of the vehicle. All essential components of the control device 2 are preferably provided on a printed circuit board 7. These components also include a relay 8 or a corresponding switching means (e.g., thyristor, MOSFET (Metal-Oxide Semiconductor Field-Effect Transistor), etc.), which is preferably integrated via an electric connection 9 in the electric circuit/control circuit of the starter 19 for starting the engine. For example, relay 8 may thus be connected in the form of an on-off switch in series with the starter, with the starter relay or with a corresponding component of the starting electronic system. Consequently, the engine of the vehicle can be started only if relay 8 is "switched on," i.e., closed. As was mentioned above, it is obvious to the person skilled in the art that other switching means, for example, power transistors, thyristors, MOSFETs, etc., may also be provided instead of relay 8. Furthermore, it is not absolutely necessary for the relay 8 to be integrated in the power supply circuit of the starter or of the starter relay of the vehicle engine. Other configurations are also possible depending on the type of engine and the type of engine control. The only thing that is decisive is that the engine can be prevented from being started by means of relay 8 or a corresponding switching means. Thus, the control device 2 may also be part of the starting electronic system, in which case the relay/switching means 8 is embodied by a relevant switching element of the starting electronic system.

In addition, a breath alcohol tester 4 is electrically connected to the control device 2. The breath alcohol tester 4 is preferably in the form of a hand-held device 4. For example, the hand-held device may be a "Dräger Interlock XT"(™) hand-held device, which is connected to the control device 2 via a power cable or data cable 10. However, the connection may also be a wireless connection, for example, by means of infrared light, Bluetooth, etc. The hand-held device 4 usually has a replaceable mouthpiece, which is connected to an alcohol sensor. Furthermore, a display as well as a plurality of operating buttons may be provided. The alcohol sensor may be connected to an electronic analyzing unit in order to determine the alcohol level from the measured breath alcohol concentration.

If a driver would like to start his or her vehicle equipped with an interlock system, the driver must first turn on the ignition by means of the ignition key. The prompt to blow into the mouthpiece of the hand-held device 4 will thereupon appear on the display of the hand-held device 4 (an acoustic signal may additionally sound). The breath alcohol concentration or alcohol level is now measured by means of the alcohol sensor. If this alcohol level is within the defined limit range, there will be a release, which is displayed by a message on the display screen of the hand-held device (an acoustic signal may additionally sound in this case as well). The driver can subsequently start the engine by means of the ignition key. During the testing of the alcohol concentration/alcohol level, the alcohol sensor or electronic analyzing unit generates a signal, which is transmitted from the hand-held device 4 via the data cable 10 to the control device. If the measured breath alcohol concentration or alcohol level is within the defined limits, the control device (analyzing unit) 21 of the control device 2 generates a corresponding control signal for "switching on" relay 8 in the ignition circuit between the battery and the starter. If the measured concentration is outside these limits, relay 8 remains switched off, as a result of which the engine is prevented from being started. The defined limit range, within which starting of the engine is permissible, is stored in a memory in the control device itself or in the hand-held device and can be set permanently and, of course, also modified by an authorized person or by an authorized institution. Furthermore, all relevant data, i.e., the point of time at which the attempt at starting the engine was made, the measured breath alcohol concentration, possible attempts at tampering, etc., are likewise stored in a memory in the control device 2 or in the hand-held device 4 and can be read by the authorized person or institution. Data can be entered and read by means of a data cable, which is connected to the control device 2 or to the hand-held device 4, or also in a wireless manner, which will be explained in detail below.

As can be seen in FIG. 1, the control device 2 is provided with an interface, which can be coupled with a data connector 11. The data connector is connected via a data cable 12 to another data connector 13, which can be coupled with an interface of module 3.

Module 3 is preferably a component separate from the control device 2 but it may be preferably mechanically coupled with the housing of the control device. It is conceivable, furthermore, that the interfaces of the control device or of the module are designed as male/female plug type connections, so that the control device and the module can be coupled with one another electrically directly without the use of the data cable. However, the connection between the control device and the module may also be designed by means of one or more terminals or similar types of connection in order to keep the effort needed for installation in the service workshop as low as possible. Furthermore, it is possible for the control device 2 and the module 3 to be embodied on a common printed circuit board 22, which is mounted in a "common" housing. The coupling between the hand-held device 4 and the control device/module 2, 3 is preferably brought about in a wireless manner in this case because the housing in which the control device 2 and the module 3 are contained in an integrated form is preferably mounted permanently in the interior of the vehicle (for example, under the dashboard or in the engine compartment).

Module 3 contains all the essential components for a cableless data transmission from/to a remotely located control system 20 (for example, computer/server/cell phone of an authorized person or institution) as well as an additional relay (transceiver module switching device) 14 to bypass relay 8 of the control device 2 of the interlock system 1 in case of a technical malfunction. The electric connection (represented as connectors 11, 13 and data cable 12) between the control device 2 and module 3 contains at least one power supply unit, a data line as well as two cables, by means of which relay 14 is connected in parallel with relay 8 of the control device to bypass relay 8.

The components for the cableless data transmission (for example, via UMTS (Universal Mobile Telephony System/ Service), GSM (Global System for Mobile Communications), GPRS (General Packet Radio Service), etc.) are generally represented by a "transmitter/receiver" block 15

(hereinafter called "transceiver" for short). Reading of a memory 16 in the transceiver module 3 or of a memory 17 in the control device 2 (completely or partially) is made possible by means of the transceiver module 3 without a service workshop having to be visited for this. Memory 16 may be located in the module (as shown) or in the control device 2 (memory 17), the data transmission from the control device 2 to the module 3 taking place in the latter case via the data line(s) of the data cable 12. The communications protocols necessary for the data transmission depend on the type of communication used (UMTS, GSM, GPRS, etc.) and are known to the person skilled in the art. The data transmission may take place at regular intervals, triggered by a certain event (e.g., a breath test performed without a time interval, a certain number of breath tests above a defined limit value, an attempt at tampering recorded by the interlock, the expiration of a service or calibration period, etc.), or it may be triggered with a signal (e.g., by SMS or by another suitable protocol) to the interlock system or to module 3.

The data are now transmitted from memory 16 or 17 of the interlock system to a target system (control system, data management system, etc.). The data are stored and possibly processed in this target system.

Regardless of the transmission of data from memory 16 or 17, a notification can be sent from the interlock system 1 directly to the regulatory person in charge (or to the institution in charge) (e.g., to a cell phone or via e-mail/fax) in case of misconduct of the driver (failure to pass an alcohol test, attempt at tampering, etc.).

As is shown in FIG. 1 and as was explained above, module 3 is connected to the control device 2 of the interlock system 1 by means of a data cable 12 or another suitable connection. The supply voltage for the module 3 is tapped, via a supply voltage bypass circuit, directly at a point in front of the tapping of the supply voltage for the electronic unit of the control device 2 at terminals 5 and 6. This means that the control device 2 of the interlock system and module 3 for the wireless data transmission are connected in parallel to one another in the preferred exemplary embodiment shown. This parallel connection brings about a power supply for the module 3 that is independent from the control device and thus guarantees functioning of the module 3 even in case of complete technical defect of the control device 2.

In the embodiment of the interlock system shown, a so-called release relay 8, which interrupts the connection between the ignition lock and the starter of the engine until a valid breath alcohol concentration test with a test result that permits release of the starting operation has been performed, is provided in the control device 2. In case of a defect of the interlock system 1, especially of the control device 2, the situation may occur that relay 8 cannot switch any more and the driver is therefore no longer able to start the engine of his or her vehicle. This state is eliminated with the "safety relay" 14 described, which is part of module 3 and is connected in parallel to the release relay 8 proper of the interlock system.

This OR connection of the two relays 8 and 14 makes it possible to bypass a blocking interlock system by the safety relay 14 being closed. The safety relay 14 is triggered here by means of wireless data transmission between module 3 and the remotely located control system. Two preferred embodiments are conceivable in this connection. In one embodiment, module 3 has a transmitter/receiver (transceiver) in the form of a cell phone submodule 15. Module 3 is thus able, for example, to receive an SMS (short message service) and to check the sender of this SMS as well as the contents of the SMS. The driver of the vehicle must report in this embodiment to a person/agency authorized to effect release. This agency is, for example, the probation officer, employer or another institution. This agency now sends an SMS with a release code to the cell phone submodule 15 of the interlock system 3, for example, via an aforementioned cell phone. The executable software being stored in module 3 then checks whether the release code and the transmitting cell phone are authorized. Methods that are known to the person skilled in the art and do not need to be explained in more detail here are used for this. When the authorization of the release code has been recognized and confirmed, module 3 then bypasses the interruption of the starter circuit by means of safety relay 14 by the safety relay 14 connected in parallel to the "defective" or opened release relay 8 being closed.

As soon as the interlock system or relay 8 is bypassed by means of module 3, i.e., by means of relay 14, an entry is made into memory 17 of the interlock system or an entry is made into memory 16 (if this is still allowed by the defect of the control device) via the data line to the control device of the interlock system in order for this bypassing to be recorded as an "authorized access." As is obvious from the above explanations, a memory 16 may be provided directly in module 3 and/or a memory 17 may be provided in the control device 2 itself.

The release code is transmitted by means of GPRS (General Packet Radio Service) in another preferred embodiment. The quantity of information transmitted in one packet is potentially greater with the use of GPRS, and it is therefore possible to transmit not only a release code of practically any desired length but also additional information. This information includes, among other things, the time limitation of the bypassing.

The wireless data transmission makes it, furthermore, possible to perform "remote maintenance," i.e., self-tests of the interlock system or resetting of timers or blocks (e.g., if the interlock was set into a "lockout mode" after violations, which no longer permits restart of the vehicle). Moreover, service data in the interlock memory 16 and/or 17 as well as parameter settings (e.g., limit values, etc.) can be read and overwritten and updates of the device software can be performed.

The alcohol tester 4 was described above as a breath alcohol tester. However, a "transcutaneous" alcohol tester, which is attached to a body part of the person to be monitored, may also be used instead of this breath alcohol tester. Continuous checking of the blood alcohol level can be performed by means of such a tester even during the operation of the vehicle. This tester may be carried concealed on the body, for example, on the leg of the person, where it is covered by the pants. It is also advantageous to arrange the tester on the right forearm. A wireless transmission path is advantageously provided between the transcutaneous alcohol tester and the control device, which contains the analyzing unit belonging to it. Transmission systems that operate optically, magnetically or with high frequency are suitable for this. It is advantageous in this connection to design the transmission path as a bidirectional path in order to make a mutual data communication possible between the transcutaneous tester and the analyzing unit of the interlock system.

While specific embodiments of the invention have been described in detail to illustrate the application of the principles of the invention, it will be understood that the invention may be embodied otherwise without departing from such principles.

What is claimed is:

1. An interlock system for a vehicle, the interlock system comprising:
an alcohol tester for measuring an alcohol level of a driver of the vehicle;
a control device coupled with said alcohol tester for allowing starting of the vehicle or preventing the vehicle from being started depending on the measured alcohol level; and
a transceiver module coupled with said control device for sending data to a remotely located control system in a wireless manner and for receiving data in a wireless manner, said transceiver module releasing said control device in response to data received in a wireless manner in order to allow starting of the vehicle regardless of an operating state of said control device, said control device having a switching device coupled with a starter of the vehicle, said switching device being switched by means of an analyzing unit of said control device depending on the measured alcohol level, said transceiver module having a transceiver module switching device connected in parallel to said switching device of said control device, said transceiver module switching device being switched in response to data received in a wireless manner.

2. An interlock system in accordance with claim 1, wherein said alcohol tester is a breath alcohol tester comprising a hand-held device connected to said control device via an electric cable.

3. An interlock system in accordance with claim 1, wherein said control device turns on or blocks a power supply to the starter of the vehicle depending on the measured alcohol level.

4. An interlock system in accordance with claim 1, wherein said transceiver module is connected to said control device via an electric cable, wherein said electric cable has at least one data line, power supply lines and lines for bypassing said switching device provided in said control device and coupled with the starter of the vehicle.

5. An interlock system in accordance with claim 1, wherein at least one of said transceiver module and said control device have a memory written to and read by means of wireless data transmission.

6. An interlock system in accordance with claim 1, wherein said transceiver module releasing said control device in response to data received in a wireless manner has a time limitation or a duration of release is reported to said transceiver module by means of data transmitted in a wireless manner.

7. An interlock system in accordance with claim 1, wherein maintenance of the interlock system and/or a self-test of the interlock system can be performed by means of wireless data transmission, wherein the result of the self-test and/or individual checked values are transmitted to said control system in a wireless manner.

8. An interlock system in accordance with claim 1, wherein parameter settings of the interlock system can be modified and/or software updates of the interlock system can be performed by means of wireless data transmission.

9. An interlock system in accordance with claim 1, wherein said wireless data transmission takes place at regular intervals or is triggered by a certain event.

10. An interlock system in accordance with claim 1, wherein said control device and said transceiver module are embodied on a common printed circuit board.

11. An interlock system in accordance with claim 1, wherein said transceiver module is coupled directly with said control device and is electrically connected to said control device by means of corresponding connections.

12. An interlock system for a vehicle, the interlock system comprising:
an alcohol tester for measuring an alcohol level of a driver of the vehicle;
a control device coupled with said alcohol tester for allowing starting of the vehicle or preventing the vehicle from being started depending on the measured alcohol level; and
a transceiver module coupled with said control device for sending data to a remotely located control system in a wireless manner and for receiving data in a wireless manner, said transceiver module releasing said control device in response to data received in a wireless manner in order to allow starting of the vehicle regardless of an operating state of said control device, wherein said transceiver module is supplied with voltage independently from said control device in order to be able to release said control device in case of a technical defect of said control device in response to data transmitted to said transceiver module in a wireless manner.

13. An interlock system for a vehicle, the interlock system comprising:
an alcohol tester for measuring an alcohol level of a driver of the vehicle;
a control device coupled with said alcohol tester for allowing starting of the vehicle or preventing the vehicle from being started depending on the measured alcohol level; and
a transceiver module coupled with said control device for sending data to a remotely located control system in a wireless manner and for receiving data in a wireless manner, said transceiver module releasing said control device in response to data received in a wireless manner in order to allow starting of the vehicle regardless of an operating state of said control device wherein said control device has a semiconductor switching means coupled with a starter of the vehicle, said semiconductor switching means being switched by means of an analyzing unit of said control device depending on the measured alcohol level, said semiconductor switching means comprising one or more power transistors, thyristors or MOSFETs.

14. An interlock system in accordance with claim 13, wherein said transceiver module comprises a transceiver module semiconductor switching means connected in parallel to said semiconductor switching means of said control device, said transceiver module semiconductor switching means being switched in response to data received in a wireless manner.

15. An interlock system for a vehicle with a battery and a starter and an ignition circuit between the battery and the starter, the interlock system comprising:
an alcohol tester for measuring an alcohol level of a driver of the vehicle;
a control device coupled with said alcohol tester and with a switching device in said ignition circuit with an off switch state preventing the vehicle from being started and a switched on state for allowing starting of the vehicle, said control device changing the state of said switching device depending on the measured alcohol level;
a supply voltage bypass circuit electrically connected to the battery and electrically connected to the starter and bypassing said control device; and a transceiver module coupled with said control device for sending data from said control device to a remotely located control system in a wireless manner and for receiving data in a wireless manner, said transceiver module including a transceiver module switching device in said supply voltage bypass circuit with an off switch state blocking current flow in said supply voltage bypass circuit from the battery to the starter and a switched on state not blocking current flow in said supply voltage bypass circuit from the battery to the starter for allowing starting of the vehicle, said transceiver module switching device assuming said switched on state in response to data received in a wireless manner in order to allow starting of the vehicle regardless of the operating state of said control device.

16. An interlock system in accordance with claim 15, wherein:
    said alcohol tester is a breath alcohol tester comprising a hand-held device connected to said control device via an electric cable; and
    said control device turns on or blocks a power supply to a starter of the vehicle depending on the measured alcohol level.

17. An interlock system in accordance with claim 16, wherein:
    said switching device of said control device has a relay coupled with the starter of the vehicle, said relay being switched by means of an analyzing unit of said control device depending on the measured alcohol level; and
    said transceiver module switching device has a transceiver module relay in said supply voltage bypass circuit connected in parallel to said relay of said control device, said transceiver module relay being switched in response to data received in a wireless manner.

18. An interlock system in accordance with claim 17, wherein said transceiver module is connected to said control device via an electric cable, wherein said electric cable has at least one data line, power supply lines and lines for bypassing the relay provided in said control device, coupled with the starter of the vehicle and forming said supply voltage bypass circuit.

19. An interlock system in accordance with claim 18, wherein at least one of said transceiver module and said control device have a memory written to and read by means of wireless data transmission.

20. An interlock system for a vehicle, the interlock system comprising:
    an alcohol tester for measuring an alcohol level of a driver of the vehicle;
    a control device coupled with said alcohol tester for allowing starting of the vehicle or preventing the vehicle from being started depending on the measured alcohol level; and
    a transceiver module coupled with said control device for sending data to a remotely located control system in a wireless manner and for receiving data in a wireless manner, said transceiver module releasing said control device in response to data received in a wireless manner in order to allow starting of the vehicle regardless of an operating state of said control device, said transceiver module being connected to said control device via an electric cable, said electric cable having at least one data line, power supply lines and lines for bypassing a relay provided in said control device and coupled with a starter of the vehicle.

* * * * *